US00PP33077P2

(12) United States Plant Patent
Geerlings

(10) Patent No.: US PP33,077 P2
(45) Date of Patent: May 18, 2021

(54) ***PHLOX* PLANT NAMED 'OLYMPUS'**

(50) Latin Name: *Phlox paniculata*
Varietal Denomination: Olympus

(71) Applicant: Peter Geerlings, Hillegom (NL)

(72) Inventor: Peter Geerlings, Hillegom (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/974,011

(22) Filed: Sep. 5, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Phlox* plant named 'Olympus', characterized by its broadly upright plant habit; freely branching habit; thick green and light yellow variegated leaves that are tinged with red; freely flowering habit; long flowering period; relatively large purple-colored flowers with white-colored centers; and good garden performance.

2 Drawing Sheets

Botanical designation: *Phlox paniculata.*
Cultivar denomination: 'OLYMPUS'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox paniculata* and hereinafter referred to by the cultivar name 'Olympus'.

The new *Phlox* plant is a product of a planned breeding program conducted by the Inventor in Hillegom, The Netherlands. The objective of the breeding program was to create new uniform and freely flowering *Phlox* plants with unique and attractive leaf and flower coloration.

The new *Phlox* plant originated from an open-pollination in 2012 in Hillegom, The Netherlands, of *Phlox paniculata* 'Pixie Miracle', not patented, as the female, or seed, parent with an unknown *Phlox paniculata* seedling selection as the male, or pollen, parent. The new *Phlox* plant was discovered and selected by the Inventor as a single flowering plant from within the progeny of the stated open-pollination in a controlled greenhouse environment in Hillegom, The Netherlands in July, 2014.

Asexual reproduction of the new *Phlox* plant by vegetative cuttings in a controlled greenhouse environment in Hillegom, The Netherlands since February, 2015, has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Olympus'. These characteristics in combination distinguish 'Olympus' as a new and distinct *Phlox* plant:

1. Broadly upright plant habit.
2. Freely branching habit.
3. Thick green and light yellow variegated leaves that are tinged with red.
4. Freely flowering habit.
5. Long flowering period.
6. Relatively large purple-colored flowers with white-colored centers.
7. Good garden performance.

Plants of the new *Phlox* differ primarily from plants of the female parent, 'Pixie Miracle', in the following characteristics:

1. Plants of the new *Phlox* are taller than plants of 'Pixie Miracle'.
2. Plants of the new *Phlox* are more freely branching than plants of 'Pixie Miracle'.
3. Leaves of plants of the new *Phlox* are green and yellow variegated and tinged with red in color whereas leaves of plants of 'Pixie Miracle' are solid green in color.
4. Flowers of plants of the new *Phlox* are purple in color with white-colored centers whereas flowers of plants of 'Pixie Miracle' are lavender in color with bright white-colored centers.

Plants of the new *Phlox* can also be compared to plants of *Phlox paniculata* 'Nora Leigh', not patented. In side-by-side comparisons conducted in Hillegom, The Netherlands, plants of the new *Phlox* and 'Nora Leigh' differed primarily in the following characteristics:

1. Plants of the new *Phlox* are shorter than plants of 'Nora Leigh'.
2. Leaves of the new *Phlox* are thicker than leaves of plants of 'Nora Leigh'.
3. Leaves of plants of the new *Phlox* are green and yellow variegated and tinged with red in color whereas leaves of plants of 'Nora Leigh' are green and white variegated in color.
4. Flowers of the new *Phlox* are larger than flowers of plants of 'Nora Leigh'.
5. Flowers of plants of the new *Phlox* are purple in color with white-colored centers whereas flowers of plants of 'Nora Leigh' are white in color with pinkish red-colored centers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet is a side perspective view of a typical flowering plant of 'Olympus' grown in a container.

The photograph on the second sheet is a close-up view of a typical flowering plant of 'Olympus'.

DETAILED BOTANICAL DESCRIPTION

The aforementioned photographs and following observations, measurements and values describe plants grown during the summer in an outdoor nursery in Hillegom, The Netherlands and under commercial practices typical of commercial *Phlox* production. During the production of the plants, day temperatures ranged from 20° C. to 35° C. and night temperatures ranged from 12° C. to 22° C. Plants were six months old when the photographs and description were taken. In the following description, color references are made to The Royal Horticultural Society Colour Chart, 2015 Edition, except where general terms of ordinary dictionary significance are used.

Botanical classification: *Phlox paniculata* 'Olympus'.

Parentage:

*Female, or seed, parent.*—*Phlox paniculata* 'Pixie Miracle', not patented.

*Male, or pollen, parent.*—Unnamed proprietary seedling selection of *Phlox paniculata*, not patented.

Propagation:

*Type.*—By vegetative cuttings.

*Time to initiate roots, summer.*—About three weeks at temperatures about 20° C.

*Root description.*—Fine, moderately fibrous; typically, close to 158B to 158C in color, actual color of the roots is dependent on substrate composition, water quality, fertilizer type and formulation.

*Rooting habit.*—Freely branching; medium density.

Plant description:

*Plant and growth habit.*—Broadly upright plant habit; overall plant shape, obovate inverted triangle; basally branching habit; moderately vigorous growth habit and moderate growth rate.

*Plant height, soil level to top of floral plane.*—About 40.9 cm.

*Plant height, soil level to top of foliar plane.*—About 29.5 cm.

*Plant width (spread).*—About 21.9 cm.

*Lateral branches.*—Length: About 23.2 cm. Diameter: About 6 mm. Internode length: About 2.3 cm. Strength: Strong. Aspect: Mostly erect. Texture and luster: Smooth, glabrous; moderately glossy. Color, developing: Close to N77B tinged with close to 145B. Color, developed: Close to between N77B and N79D tinged with close to between 144C and 145A; at the internodes, close to between 144C and 145A.

Leaf description:

*Arrangement and quantity.*—Opposite, simple; about 22 per lateral branch.

*Length.*—About 13.5 cm.

*Width.*—About 3.8 cm.

*Shape.*—Elliptic; moderately carinate; thick.

*Apex.*—Acute.

*Base.*—Narrowly truncate.

*Margin.*—Entire; moderately undulate and moderately revolute.

*Texture and luster, upper surface.*—Smooth, glabrous; slightly leathery; slightly glossy.

*Texture and luster, lower surface.*—Smooth, glabrous; slightly leathery; matte.

*Venation pattern.*—Pinnate.

*Color.*—Developing leaves, upper surface: Close to between 77A and N77B; midvein and area surrounding midvein, close to NN137A. Developing leaves, lower surface: Close to N77B; midvein, close to 146C; area surrounding midvein, close to 138A to 138B. Fully expanded leaves, upper surface: Close to NN137A to NN137D; towards the margins, close to 8C, 10C and 11C; occasionally slightly to moderately tinged with close to 185C to 185D; venation, close to 144A to 144B. Fully expanded leaves, lower surface: Close to between 147B and 191A; towards the margins, close to 9D and 10C; occasionally slightly tinged with close to 185D; venation, close to 146C.

*Petioles.*—Length: About 3 mm. Diameter: About 2.5 mm by 3 mm. Strength: Strong. Texture and luster, upper and lower surfaces: Smooth, glabrous; slightly glossy. Color, upper surface: Close to 144B slightly to strongly tinged with close to N77A. Color, lower surface: Close to 144C.

Flower description:

*Flower type and flowering habit.*—Single rotate salverform flowers arranged in panicles; flowers face upright and outward; panicles roughly conical in shape; freely flowering habit with about 500 flowers developing per inflorescence.

*Fragrance.*—Faintly to moderately fragrant; sweet and pleasant.

*Natural flowering season.*—Long flowering period; plants flower continuously from mid to late summer in The Netherlands.

*Postproduction longevity*.—Flowers last about ten days on the plant; flowers not persistent.

*Flower buds*.—Height: About 1.8 cm. Diameter: About 5 mm. Shape: Oblanceolate. Texture and luster: Smooth, glabrous; matte. Color: Sepals, close to N77B and proximally, close to 149D; petals, close to N88B.

*Inflorescence height*.—About 19.2 cm.

*Inflorescence diameter*.—About 18.1 cm.

*Flower diameter*.—About 3.1 cm.

*Flower depth*.—About 2.8 cm.

*Flower throat diameter*.—About 3 mm.

*Flower tube length*.—About 2.1 cm.

*Flower tube diameter*.—About 3 mm.

*Petals*.—Quantity per flower: Typically five in a single whorl; lower 55% to 60% of petals fused and forming a narrow tube; somewhat imbricate. Length: About 3.7 cm. Width: About 1.8 cm. Shape: Spatulate. Apex: Rounded. Margin: Entire; moderately undulate. Texture and luster, upper surface: Smooth, glabrous; velvety; matte. Texture and luster, lower surface: Smooth, glabrous; moderately velvety; slightly glossy. Texture and luster, throat: Smooth, glabrous; moderately velvety; matte. Texture and luster, tube: Moderately pubescent; matte. Color: Developing petals, upper surface: Close to N87C to N87D; towards the base, close to 157C. Developing petals, lower surface: Close to between N88B and 90C; towards the base, close to 157C. Fully developed petals, upper surface: Close to N81B to N81C; towards the base, close to N155A; venation, similar to lamina color; with development, color becoming closer to N80B to N80C and towards the base, close to 76D. Fully developed petals, lower surface: Close to 86D; towards the base, close to 85C; venation, similar to lamina color; with development, color becoming closer to N88C to N88D and towards the base, close to 85B. Throat: Close to N80B; venation, close to N80B. Tube: Close to N78A; venation, close to N87A.

*Sepals*.—Quantity per flower: Typically five in a single whorl, lower 20% fused and forming a campanulate calyx. Calyx length: About 1 cm. Calyx diameter: About 4 mm. Length: About 1 cm. Width: About 2 mm. Shape: Lanceolate. Apex: Long and narrowly apiculate. Margin: Entire, not undulate. Texture and luster, upper surface: Smooth, glabrous; matte. Texture and luster, lower surface: Smooth, glabrous; slightly glossy. Color, developing sepals, upper surface: Close to 147C; margins, close to N77B. Color, developing sepals, lower surface: Close to N77B. Color, developed sepals, upper surface: Close to 147D; margins, close to N77D; venation, close to 147A; color does not change with development. Color, developed sepals, lower surface: Close to N77B; towards the base, close to 145A to 145B; venation, similar to lamina colors; color does not change with development.

*Peduncles*.—Length, primary peduncles: About 15.8 cm. Diameter, primary peduncles: About 3 mm. Aspect, primary peduncles: Erect; secondary peduncles, about 40° from primary peduncle axis. Aspect, secondary peduncles: About 45° from vertical. Strength, primary and secondary peduncles: Strong. Texture and luster, primary and secondary peduncles: Smooth, glabrous; moderately glossy. Color, primary and secondary peduncles: Close to 148A blotched with close to 146C.

*Pedicels*.—Length: About 3 mm. Diameter: About 1 mm. Aspect: About 20° from peduncle axis. Strength: Moderately strong. Texture and luster: Smooth, glabrous; moderately glossy. Color: Close to 144B.

*Reproductive organs*.—Stamens: Quantity per flower: Typically five. Filament length: About 1 mm. Filament color: Close to NN78D. Anther size: About 2.5 mm by 0.75 mm. Anther shape: Oblong. Anther color: Close to 2D. Pollen amount: Moderate. Pollen color: Close to 8D. Pistils: Quantity per flower: One. Pistil length: About 1.9 cm. Stigma diameter: About 1 mm. Stigma shape: Cleft, three-parted. Stigma color: Close to between 145C and 149D. Style length: About 1.75 cm. Style color: Close to N77A; towards the base, close to 145C. Ovary color: Close to 144C.

*Seeds and fruits*.—To date, seed and fruit development have not been observed on plants of the new *Phlox*.

Pathogen & pest resistance: To date, plants of the *Phlox* have not been observed to be resistant to pathogens and pests common to *Phlox* plants.

Garden performance: Plants of the new *Phlox* have been observed to have good garden performance and tolerate rain, wind, high temperatures about 35° C. and to be suitable for USDA Hardiness Zones 6 through 10.

It is claimed:

1. A new and distinct *Phlox* plant named 'Olympus' as illustrated and described.

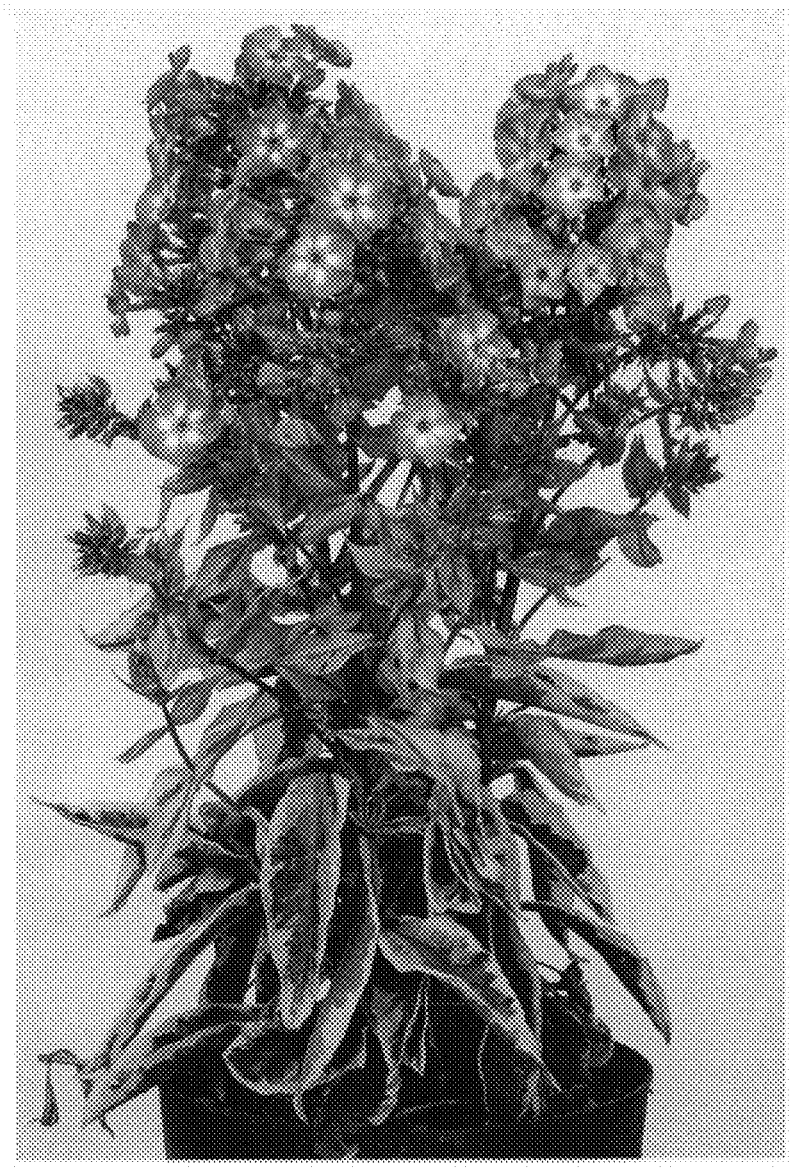

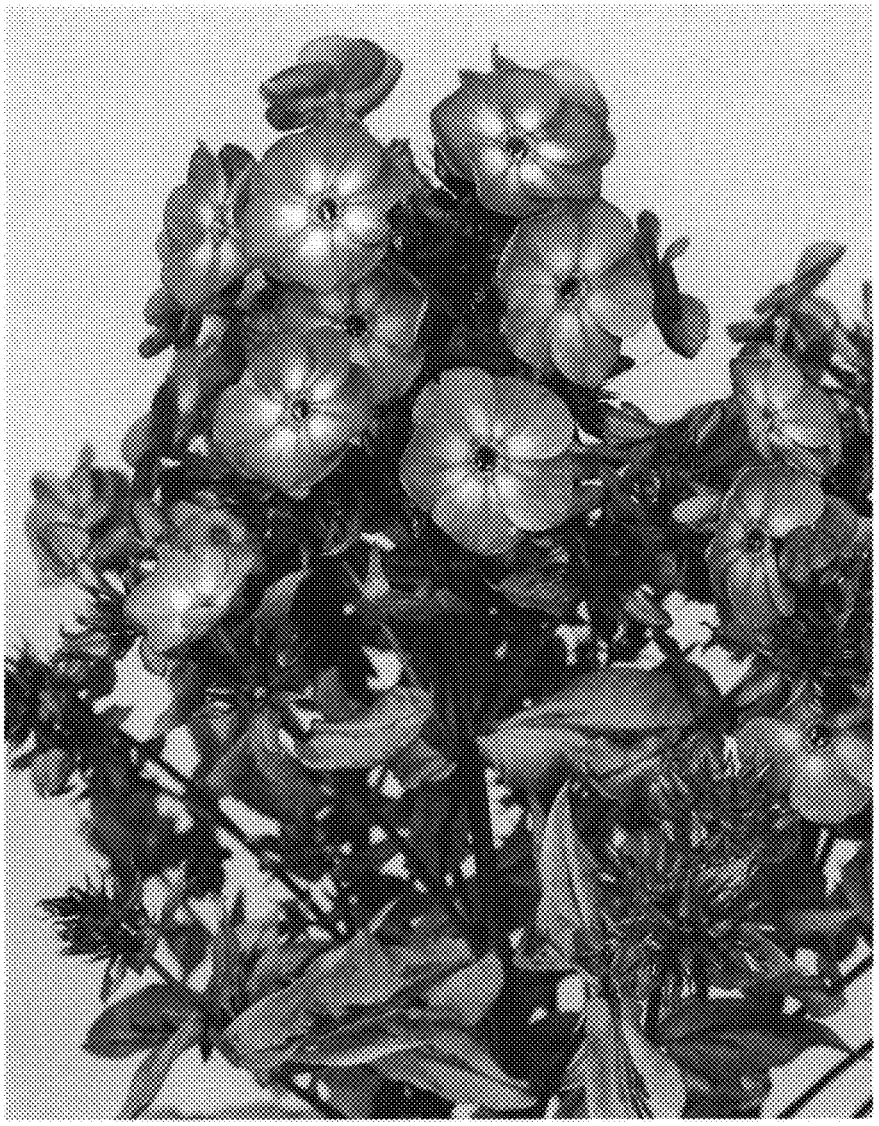

* * * * *